United States Patent [19]

Rao

[11] Patent Number: 4,474,997

[45] Date of Patent: Oct. 2, 1984

[54] OXIDATION PROCESS AND CATALYST THEREFOR

[75] Inventor: Velliyur N. M. Rao, Wilmington, Del.

[73] Assignee: E. I. Du Pont de Nemours and Company, Wilmington, Del.

[21] Appl. No.: 533,751

[22] Filed: Sep. 19, 1983

Related U.S. Application Data

[62] Division of Ser. No. 395,783, Jul. 6, 1982, Pat. No. 4,429,055.

[51] Int. Cl.$^3$ .................... C07C 45/35; C07C 45/37
[52] U.S. Cl. ................................ 568/473; 568/470; 568/475; 568/478
[58] Field of Search ............. 568/473, 475, 476, 478, 568/470, 489, 469.9

[56] References Cited

U.S. PATENT DOCUMENTS

| | | | |
|---|---|---|---|
| 2,938,001 | 5/1960 | Rosset | 252/432 |
| 3,255,238 | 6/1966 | Roelen et al. | 260/497 |
| 3,390,103 | 6/1968 | Roelen et al. | 252/432 |
| 3,398,199 | 8/1968 | Walde et al. | 568/476 |
| 4,065,507 | 12/1977 | Hardman et al. | 568/478 |
| 4,245,118 | 1/1981 | Yamamoto et al. | 568/476 |
| 4,320,031 | 3/1982 | Parthasarathy et al. | 252/432 |
| 4,381,411 | 4/1983 | Pedersen et al. | 568/470 |

FOREIGN PATENT DOCUMENTS

| | | | |
|---|---|---|---|
| 1160858 | 1/1964 | Fed. Rep. of Germany . | |
| 56-86154 | 7/1981 | Japan | 252/432 |
| 967241 | 8/1964 | United Kingdom . | |
| 1065984 | 4/1967 | United Kingdom | 252/432 |

Primary Examiner—Werren B. Lone

[57] ABSTRACT

An oxidation catalyst comprising boron phosphate impregnated with from 5 to 20 weight percent silver and its use to oxidize propylene, butene-1, butadiene-1,3 and methanol is disclosed. The oxidation takes place at from 200° to 700° C. Preferably water vapor is present.

5 Claims, No Drawings

OXIDATION PROCESS AND CATALYST THEREFOR

Cross Reference to Related Application

This application is a division of application Ser. No. 395,783 filed Jul. 6, 1982, now U.S. Pat. No. 4,429,055.

BACKGROUND OF THE INVENTION

1. Field of the Invention

The present invention relates to a process for oxidizing olefins to unsaturated aldehydes and diolefins to cyclic ethers and alcohols to aldehydes and ethers using a silver/boron phosphate catalyst.

2. Prior Art

U.S. Pat. No. 4,320,031 discloses a process of catalytic oxidation dehydrogenation of alkenes or alkadienes to furan compounds using a silver molybdate catalyst promoted with phosphorus arsenic, antimony or bismuth.

Br. No. 967,241 discloses a process for the production of $\alpha,\beta$-unsaturated aliphatic carboxylic acids from olefins using a solid phosphoric acid catalyst which has been activated with one or more of copper, silver, iron, cobalt, nickel, antimony, bismuth, molybdenum, tungsten and uranium.

German Auslegeschrift No. 1,160,858 discloses using a catalyst comprising a heavy metal oxide selected from copper oxide, silver oxide, chromium oxide, bismuth oxide, tungsten oxide and molybdenum oxide with boric acid and phosphoric acid to oxidize propylene. Acetic acid is the major product in the Examples.

SUMMARY OF THE INVENTION

The present invention relates to novel silver on boron phosphate catalysts and their use in the oxidation of methanol, propylene, butenes and butadiene under oxygen limiting conditions.

DETAILED DESCRIPTION

The catalysts of the present invention are silver impregnated on boron phosphate ($BPO_4$). They are prepared by treating boron phosphate with a solution of a silver salt in a solvent. Silver nitrate is the preferred salt because the nitrate ion is readily removed by heating the impregnated boron phosphate. The resulting slurry of boron phosphate and silver salt solution is stirred for a suitable period such as from 10 min. to 2 hours. Following stirring, the solvent is removed by evaporation. The evaporation can be done under reduced pressure if desired. Following removal of the solvent, the catalyst is calcined in air using a gradual heat-up. If needed, the calcined catalyst can be reduced using hydrogen diluted with an inert gas such as nitrogen. Generally, the catalyst will contain from 5 to 20 percent by weight, based on boron phosphate, of silver. The resulting catalyst is in the form of a powder and it can be used either as the powder or it can be pelletized or granulated and the pellets or granules used.

The catalyst is most useful for oxidizing propylene, butenes, butadiene-1,3 and methanol. When oxidizing propylene, the predominant product is acrolein. When oxidizing butene-1, the predominant product is a mixture of methyl vinyl ketone and methyl ethyl ketone. When oxidizing butadiene-1,3, the predominant product is furan and hydrogenated furans such as dihydrofuran and tetrahydrofuran. When oxidizing methanol, the predominant products are formaldehyde and dimethyl ether. Depending on the starting material, the amount of oxygen in the feed stream should be from 0.05 to 0.5 atom of oxygen per atom of starting material. Generally, the oxidation reaction is carried out at from 200° to 700° C., with from 300° to 500° C. being the preferred range for oxidizing the olefins and from 500° to 600° C. being the preferred range when methanol is the starting material.

Generally, the residence time when the material being oxidized is in contact with the catalyst is from 0.01 to 2 seconds with from 0.1 to 0.4 seconds being the preferred range.

The oxygen used generally will be diluted with an inert gas such as nitrogen or helium. Generally, air is a satisfactory source of oxygen. In some instances, it may be desired to further dilute the air with nitrogen or helium.

In an especially preferred aspect of the invention, water vapor is incorporated in the feed stream. The water vapor serves to moderate the catalyst and thus improve both the conversion of the feedstock as well as the selectivity of the catalyst.

EXAMPLE 1

Catalyst Preparation I

In a 250 ml round bottom flask is placed 20 g of powdered boron phosphate. To this is added a solution of 3.4 g silver nitrate dissolved in 100 ml of acetonitrile solvent. The slurry is stirred at room temperature for ½ hour. The solvent is then removed under reduced pressure.

The resulting whitish powder is then charged into a quartz tube and heated to 200° C. and maintained at that temperature for 2 hours with a current of air going through. The temperature is raised over a period of about ½ hour to 500° C. and kept at that temperature for 1 hour, after which the temperature is raised to 600° C. and kept at this temperature for 2 hours. The resulting $Ag/BPO_4$ catalyst is allowed to cool resulting in a slightly greyish, coarse powder. The catalyst can be used as such or in granular or pellet form in actual experimental evaluations.

EXAMPLE 2

Oxidation of Propylene

A 10 mm inside diameter quartz tube is charged with a 1" (0.025 m) bed depth of the catalyst prepared as in Example 1 (as a coarse powder). The catalyst bed is heated externally using a band heater to 350° to 400° C.

A mixture of helium, air and propylene (3:2:2) is passed through this bed and the products leaving the reactor are analyzed by gas chromatography. The principal product besides unconverted starting material is acrolein. Small amounts of CO and $CO_2$ are also observed.

Oxidation of Propylene Using Metallic Silver

Using the same reaction set up, a 1" bed depth of granular silver catalyst which passes a 20 mesh screen and is retained on a 30 mesh (U.S. sieve series) screen is evaluated as a catalyst under similar operating conditions. Only traces of acrolein are observed.

Using Boron Phosphate

Plain, powdered and granular boron phosphate is also evaluated under same conditions as above. Again, only traces of acrolein are found.

EXAMPLE 3

Catalyst Preparation II

The catalyst was prepared as in Example 1 except as follows. After heat treatment in air at 600° C., the catalyst is allowed to cool in a stream of nitrogen. After all oxygen is purged, the catalyst is heated in a stream of nitrogen and hydrogen (90:10) for 1 hour at 100° C., 1 hour at 300° C. and 1 hour at 500° C. It is then cooled in a stream of nitrogen. The catalyst so prepared is greenish rather than greyish.

EXAMPLE 4

To a 5 inch (0.127 m) long stainless steel tube having an inside diameter of ⅜" (0.0095 m) is charged 9.5 g of the catalyst prepared as in Example 1. The catalyst bed is maintained at 400° C. using an external fluidized sand bed. The flow rates (as measured at standard temperature and pressure) to the catalyst bed are: propylene 63.2 cc/min., air 33.3 cc/min. and nitrogen 56.3 cc/min. The off gases are analyzed by gas chromatography. Propylene conversion is 46.1% based on oxygen in the feed and the selectivity for acrolein is 28.8%.

EXAMPLE 5

Example 4 is repeated except the temperature is 500° C. and the total flow rate (as measured at standard temperature and pressure) to the catalyst bed is about 150 cc/min. which contains 41.3% by volume propylene, 10% by volume water vapor, 21.8% by volume air and 26.9% by volume nitrogen. The conversion of propylene based on oxygen in the feed is 94.7% and the selectivity for acrolein is 81.8%.

EXAMPLE 6

Example 4 is repeated except the temperature is 500° C. and the total flow to the catalyst bed (as measured at standard temperature and pressure) is 266.1 cc/min. which contained by volume 37.6% propylene, 19.8% air, 33.5% nitrogen and 9.1% water vapor. The conversion based on oxygen in the feed is 94.9% and the acrolein selectivity is 73.9%.

EXAMPLE 7

Oxidation of Butadiene

Example 4 is repeated except 25.0 g of catalyst is used, the temperature is 500° C. and the total flow to the catalyst bed (as measured at standard temperature and pressure) is 100 ml/min. which contains by volume 27.6 parts butadiene, 25 parts air, 25.0 parts water vapor and 22.4 parts nitrogen. The conversion of butadiene based on oxygen in the feed is 90.9%. The selectivity to furan is 22.4% and to acrolein is 5.1%. Gas chromatography analysis shows two other peaks besides furan and acrolein. They have retention times the same as a mixture of dihydrofuran and trihydrofuran. Based on this analysis the selectivity to furan, dihydrofuran and trihydrofuran mixture is 59.6%.

EXAMPLE 8

Boron phosphate is screen pelleted to pass a 10 mesh and be retained on a 20 mesh U.S. sieve series screen, and then heated to 800° C. for 16 hours to reduce water sensitivity. Twenty-five grams of the thus prepared boron phosphate is impregnated with a solution of 3.93 g silver nitrate dissolved in 22 cc water. Excess water is removed under reduced pressure and the pellets are dried at 120° C. The catalyst is reduced in a stream of hydrogen at 300° C. for 2 hours and an additional 2 hours at 600° C. prior to use. The thus prepared catalyst is packed in a ⅜" (0.0095 m) inside diameter titanium tube. The tube is heated to 500° C. and the feed stream is passed through the heated catalyst bed at the following rates measured at standard pressure and temperature: helium 75 cc/min., oxygen 8 cc/min., butadiene 48 cc/min., and water vapor 109 cc/min. The contact time is about 0.3 seconds. The butadiene conversion is 3.1%. As based on carbon, the selectivity to furan is 33.2%, to maleic acid is 12.9%, and to monobasic acids is 9.6%.

I claim:

1. A process of oxidizing a gaseous starting material which is propylene, butene, butadiene-1,3 or methanol with from 0.05 to 0.5 atom of oxygen per atom of said gaseous starting material at from 200° to 700° C. in the presence of a catalytic amount of a catalyst comprising a boron phosphate support containing from 5 to 20 percent by weight, as based on boron phosphate, of silver and recovering an oxygen-containing product derived from said starting material.

2. The process of claim 1 wherein water vapor is present to moderate the catalyst.

3. The process of claim 2 wherein the gaseous starting material is propylene and acrolein is recovered as product.

4. The process of claim 2 wherein gaseous starting material is butadiene-1,3 and furan and hydrogenated furans are recovered as product.

5. The process of claim 2 wherein the gaseous starting material is methanol and formaldehyde is recovered as product.

* * * * *